United States Patent [19]

Hider et al.

[11] Patent Number: 5,256,676
[45] Date of Patent: Oct. 26, 1993

[54] 3-HYDROXY-PYRIDIN-4-ONES USEFUL FOR TREATING PARASITIC INFECTIONS

[75] Inventors: Robert C. Hider, Clacton; Timothy E. A. Peto, Oxford; Surinder Singh, West Croyden; Susan Whitehead, Hull, all of England

[73] Assignee: British Technology Group Limited, London, England

[21] Appl. No.: 918,080

[22] Filed: Jul. 24, 1992

[30] Foreign Application Priority Data

Apr. 27, 1992 [GB] United Kingdom ................ 9209078

[51] Int. Cl.⁵ .................... C07D 211/74; A61K 31/44
[52] U.S. Cl. .................................... 514/348; 546/296
[58] Field of Search ......................... 546/296; 514/348

[56] References Cited

U.S. PATENT DOCUMENTS 4,908,371  3/1990  Moerker et al. ................. 514/318

FOREIGN PATENT DOCUMENTS 0397409  11/1990  European Pat. Off. ............ 546/296
8909211   5/1989  PCT Int'l Appl. ................ 514/318
9212131   7/1992  PCT Int'l Appl. ................ 514/318
2136806   9/1984  United Kingdom ............... 546/296
2136807   9/1984  United Kingdom ............... 546/296

OTHER PUBLICATIONS

Porter et al., "Iron mobilization from hepatocyte monolayer cultures by chelators: the importance of membrane permeability and the iron-binding constant", Blood, 1988, 72, 1497-1503.

Heppner et al., "Antimalarial properties of orally active iron chelators", Blood, 1988, 72, 358-361.

Brady et al., "Release of iron from ferritin molecules and their iron-cores by 3-hydroxypyridinone chelators in vitro", Journal of Inorganic Biochemistry, 1989, 35, 9-22.

Hider et al., "The inhibition of tyrosinase by pyridinones", Biochemical Journal, 1989, 257, 289-290.

Whitehead et al., "Stage-dependent effect of desferrioxamine on growth of Plasmodium falciparum in vitro", Blood, 1990, 76, 1250-1255.

Singh et al., "Uninary metabolic profiles in human and rat of 1,2-dimethyl and 1,2-diethyl-substituted 3-hydroxypyridin-4-ones", Drug. Met. and Disp., 1992, 20, 256-261.

Epemolu et al., "Chromatography of 3-hydroxypyridin-4-ones: novel orally active iron chelators", 1990, 519, 171-178.

(List continued on next page.)

Primary Examiner—Alan L. Rotman
Assistant Examiner—Zinna N. Davis
Attorney, Agent, or Firm—Nixon & Vanderhye

[57] ABSTRACT

3-Hydroxypyridin-4-ones of formula (I)

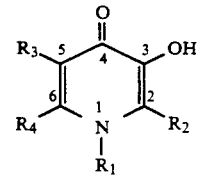

in which $R_1$ is a $C_3$ or $C_4$ hydroxyalkyl group in which the hydroxy group is terminally substituted on the alkyl group, $R_2$ is methyl or ethyl and $R_3$ and $R_4$ are each separately hydrogen, methyl or ethyl but with the proviso that the total number of carbon atoms in $R_1$ to $R_4$ is no more than six, the compound optionally being in the form of a physiologically acceptable salt and/or pro-drug thereof, are of value for the treatment of conditions caused by iron dependent parasites, particularly malaria.

10 Claims, No Drawings

OTHER PUBLICATIONS

Hershko et al., "The effect of N-alkyl modification on the antimalarial activity of 3-hydroxypyrid-4-one oral iron chelators", Blood, 1991, 77, 637-643.

Stefanini et al., "The interaction of hydroxypyridinones with human serum transferrin and ovotransferrin", Journal of Inorganic Biochemistry, 1991, 44, 27-37.

Whitehead et al., "Differences in the in vitro anti-malarial activity within the hydroxypyridin-4-one group of oral iron chelators", Abstract of presentation at 10th International Conference on Iron and Iron Proteins, 1991 (Jul. 27-31), Oxford.

Singh et al., "Development of 3-hydroxypyridin-4-ones which do not undergo extensive phase II metabolism", Poster presented at 3rd NIH sponsored symposium entitled The Development of Iron Chelators for Clinical Uses, 1992 (May 20-22), Florida.

Hershko et al., "New orally effective iron chelators", Annals of the New York Academy of Sciences, 1990, 612, 351-360.

Hider et al., "Iron chelating agents in medicine", Perspectives on Bioinorganic Chemistry, 1991, 1, 209-253.

Hider et al., "The development of hydroxypyridin-4-ones as orally active iron chelators", Annals of the New York Academy of Sciences, 1990, 612, 327-338.

3-HYDROXY-PYRIDIN-4-ONES USEFUL FOR TREATING PARASITIC INFECTIONS

This invention relates to 3-hydroxypyridin-4-one chelating agents of value in the treatment of parasitic infections and in particular to the treatment of malaria and other conditions in which the parasite is iron dependent.

Malaria parasites (Plasmodium spp.) show a complex pattern of development in the mammalian host. Infection is initiated when female mosquitoes feeding on blood inoculate sporozoites into the bloodstream from whence they enter the liver. The parasites proliferate in the liver and are ultimately released therefrom in the mature form, known as merozoites, which initiate the asexual erythrocytic cycle which causes the disease. The parasites, once taken up as merozoites by the red blood cells, pass through various stages, including the trophozoite and schizont stages, which culminate in the rupture of the blood cells with the release of much increased numbers of merozoites, thereby perpetuating the cycle.

Malaria presents a very considerable medical problem, despite the development of various drugs for its treatment. This is particularly the case since, of the different species of Plasmodium responsible for malaria in humans, P. falciparum is the species which causes the most morbidity and mortality and is at the same time the one which poses most problems by way of resistance to the preferred therapeutic agent, chloroquine.

U.S. Pat. No. 4,585,780 and various scientific papers describe the use of 3-hydroxypyridin-4-ones for the treatment of iron overload arising from various causes, particularly that arising from the treatment of pathological conditions such as thalassaemia, sickle cell anaemia, idiopathic haemochromatosis and aplastic anaemia by regular blood transfusions. Moreover, in addition to use for the treatment of general iron overload, the 3-hydroxpyridin-4-ones are of interest for use in certain pathological conditions where there may be an excess of iron deposited at certain sites even though the patient does not exhibit a general iron overload, this being the case, for example, in certain arthritic and cancerous conditions.

Although the major use described in the literature for these compounds is in the removal of iron, they are also of potential interest for the removal of other metals present in the body in deleterious amounts, for example copper, plutonium and other related transuranic metals, and especially aluminium.

The 3-hydroxypyridin-4-ones are also of interest for use in certain other contexts. Thus the free 3-hydroxypyridin-4-ones have been proposed for use in the treatment of inflammatory and atherosclerotic disease, of neoplastic disease, and as platelet anti-aggregatory agents with a role in the treatment of thrombosis. They are also of interest in various areas where chelating agents can be of value, for example in the treatment of paraquat poisoning.

Another area of use is that to which the present application particularly relates, i.e. the treatment of malaria and other parasitic infections. UK Patent Application No. 2 251 617 and its equivalents describe the finding that one group of 3-hydroxypyridin-4-ones is of particular value in the treatment of such infections since it shows a selective toxic effect on malaria infested erythrocytes, the particularly preferred compounds being substituted on the nitrogen atom of the ring by a $C_{1-3}$ aliphatic hydrocarbon group which bears a single carboxy group substituent.

The particular value of the compounds of UK Patent Application No. 2 251 617 arises from the contrast between their effect on parasite infected cells, particularly parasite infected erythrocytes, and their effect on other cells. Thus it is reported in that application, using a murine erythroleukaemia (MEL) cell line as a model for such other cells, that the compounds show a similar level of activity against malaria infected parasites to desferrioxamine and alkyl substituted 3-hydroxypyridin-4-ones such as those described by Heppner et al, Blood, 1988, 72, 358, but in contrast to those compounds these 3-hydroxypyridin-4-one carboxylic acids do not have a significant growth inhibiting effect on the MEL cell line. This means that they may be used at the quite high dosage levels required for the treatment of parasitic infections without incurring the significant level of toxic side effects experienced with compounds which do not have a selective action.

We have now found that certain of these 3-hydroxypyridin-4-one carboxylic acid compounds are formed in vivo on the metabolism of a different group of 3-hydroxypyridin-4-ones which therefore are also of considerable interest in the same context of the treatment of parasitic infections.

Accordingly the present invention comprises a method for the treatment of a patient having a condition caused by an iron dependent parasite, for example malaria, which comprises administering to that patient a therapeutically effective amount of a 3-hydroxypyridin-4-one of formula (I)

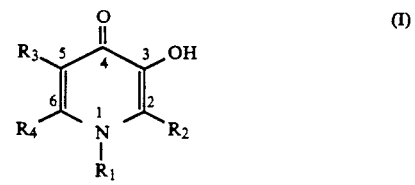

in which $R_1$ is a $C_3$ or $C_4$ hydroxyalkyl group in which the hydroxy group is terminally substituted on the alkyl group, $R_2$ is methyl or ethyl and $R_3$ and $R_4$ are each separately hydrogen, methyl or ethyl but with the proviso that the total number of carbon atoms in $R_1$ to $R_4$ is no more than six, the compound optionally being in the form of a physiologically acceptable salt and/or pro-drug thereof.

The value of the compounds of the present invention in the treatment of parasitic infections is all the more surprising in view of the disclosure by Iiershko et al., Blood, 1991, 77, 637, that the compound 3-hydroxy-2-methyl-1-(2-hydroxyethyl)pyridin-4-one was unable to suppress malaria in tests carried out in the rat. This is, however, consistent with our finding that the compounds corresponding to those of the present invention but with a group $R_1$ which is a 1-(2-hydroxyethyl) group are not metabolised to a significant extent.

However, not only do the compounds of use in the present invention have anti-parasitic activity but they also have the advantage, as compared with the compounds of UK Patent Application No. 2 251 617 that they are more lipophilic and will thus be more readily taken up from the gut into the bloodstream, where the metabolism of the hydroxymethyl group of the group $R_1$ to a carboxy group will occur. Thus, the iron chelator desferrioxamine has been used as an anti-malarial drug but this iron chelator has the disadvantage of having to be administered parenterally because it is poorly absorbed from the gastrointestinal tract and is also rapidly removed from the blood. The compounds (I) therefore further enhance the advantage which the compounds of UK Patent Application No. 2 251 617 show as compared with desferrioxamine.

It is known that iron chelators will exert an anti-malarial effect through interaction with the intracellular low molecular weight iron pool and the inhibition of ribonucleotide reductase, the ability of the drug to cross an infected cell membrane therefore being a prerequisite for anti-malarial activity, and it is believed that the 3-hydroxypyridin-4-one alcohols of the present invention are metabolised to the 3-hydroxypyridin-4-one carboxylic acids of UK Patent Application No. 2 251 617 prior to entry into the parasitized erythrocytes. Despite the charge which they carry these latter compounds have been shown to be fully capable of entering such erythrocytes and, without restriction to any particular mode of action, it is believed that it is a differential ability to enter parasitized and non-parasitized erythrocytes which forms the basis for the selective toxicity of these compounds.

As regards the $C_3$ or $C_4$ hydroxyalkyl group $R_1$, this is required to be terminally substituted, i.e. it contains a group —$CH_2OH$, and it is preferably a straight chain hydroxyalkyl group so that the groups —$(CH_2)_4OH$ and especially —$(CH_2)_3OH$ are of particular interest. Moreover, the branched $C_3$ group, —$CH(CH_3)CH_2OH$, is of rather greater interest than the branched $C_4$ groups.

As regards $R_2$ this is preferably methyl although compounds in which $R_2$ is ethyl are also of interest. There is a requirement for the total number of carbon atoms in $R_1$ to $R_4$ to be no more than six but advantageously this total is five or particularly four. Thus when $R_1$ is a $C_4$ hydroxyalkyl group there is an especial preference for $R_2$ to be methyl. Moreover, $R_3$ and $R_4$ are therefore preferably both hydrogen or one of the two is hydrogen and the other, especially $R_4$, is methyl.

Specific compounds (I) of interest are thus:
(1) 3-hydroxy-1-(3-hydroxypropyl)-2-methylpyridin-4-one;
(2) 3-hydroxy-1-(1-methyl-2-hydroxyethyl)-2-methylpyridin-4-one;
(3) 3-hydroxy-1-(4-hydroxybutyl)-2-methylpyridin-4-one;
(4) 2-ethyl-3-hydroxy-1-(3-hydroxypropyl)pyridin-4-one;
(5) 2-ethyl-3-hydroxy-1-(1-methyl-2-hydroxyethyl)-pyridin-4-one;
(6) 2-ethyl-3-hydroxy-1-(4-hydroxybutyl)pyridin-4-one; and
(7) 3-hydroxy-1-(3-hydroxypropyl)-2,6-dimethylpyridin-4-one.

The most preferred compound is compound (1) which is metabolized to the preferred compound of UK Patent Application No. 2 251 617, 1-(2-carboxyethyl)-2-methyl-3-hydroxypyridin-4-one.

It will be appreciated that certain compounds, particularly those in which $R_2$ is ethyl rather than methyl, are novel per se and are included within the scope of the present application.

The compounds may, if desired, be used in the form of a physiologically acceptable salt. These salts may be of two types, being formed with either physiologically acceptable bases or acids. Thus salts may be formed between the anion produced by the loss of the 3-hydroxy group proton and a base derived cation. Examples of suitable bases are the alkali metal hydroxides, for example sodium hydroxide, quaternary ammonium hydroxides and amines such as tris (tris representing 2-amino-2-hydroxymethyl propane 1,3-diol). More preferably, salts may be formed through protonation of the carbonyl function at the 4-position of the 3-hydroxypyridinone ring by an acid. Suitable acids may be inorganic or organic. Examples of such inorganic acids are phosphoric acid, nitric acid, sulphuric acid and particularly the hydrohalic acids hydrochloric acid, hydrobromic acid and hydroiodic acid. Examples of such organic acids are citric acid, oxalic acid, fumaric acid, maleic acid, lactic acid, succinic acid, malic acid, tartaric acid and methane sulphonic acid.

Alternatively, or additionally, the compounds may be in the form of a pro-drug, in particular a pro-drug in which the 3-hydroxy group is in the form of another group which is reconverted thereto in vivo. Such a pro-drug group may, for example, be as described in U.S. Pat. No. 4,908,371, in particular being a group R'COO wherein R' is a $C_{1-8}$ alkyl group, especially a $C_{3-7}$ group which is branched at the carbon atom adjacent to the carbonyl group, such as an isopropyl or t-butyl group.

It will be appreciated that certain of the non-preferred groups $R_1$ contain an asymmetric carbon atom and the compound (I) can therefore exist in optically active forms. Compounds containing the preferred groups $R_1$ have the additional advantage of not requiring stereospecific synthesis or the separation of a mixture of isomers in order to produce an isomer-free product.

The compounds (I) may be prepared by procedures such as those described in U.S. Pat. No. 4,585,780 and by variations thereon which will be apparent to those skilled in the art. In particular a corresponding 3-hydroxy-4-pyrone can be reacted with a compound $R'NH_2$ in which R' represents the group present on the nitrogen atom of the desired compound or a group convertible thereto, the reaction being carried out in the presence of a base, for example an alkali metal hydroxide such as sodium hydroxide. This procedure is specifically exemplified in Examples 12 and 13 of U.S. Pat. No. 4,585,780 for the preparation from maltol of 1-(3-hydroxypropyl)-3-hydroxy-2-methyl-pyridin-4-one and its 1-(4-hydroxybutyl) analogue, which are obtained by the procedure described in the patent in the form of the hydrobromide, and may be applied in an exactly analogous fashion to the preparation of other anti-parasitic compounds of use in the present invention having alternative groups $R_1$ to $R_4$.

Other 3-hydroxy-4-pyrone starting materials than maltol are readily available, for example as described in published U.S. Pat. application Ser. No. 310,141 (series of 1960) or otherwise.

An alternative general route involves nucleophilic substitution at the nitrogen atom of the corresponding 3,4-dihydroxypyridine (or 3-hydroxypyridin-4-one), for example using an organic halide R'X in which R' represents the group present on the nitrogen atom of the desired compound or a group convertible thereto. Yet another route involves reaction of the corresponding 3-hydroxypyridin-4-one with an amine $R'NH_2$ in which R' represents the group present on the nitrogen atom of the desired compound or a group convertible thereto.

In most cases it will be appropriate to protect the 3-hydroxy group in the reactant 3-hydroxypyrone or 3-hydroxypyridinone precursor. A common form of protection is to convert the 3-hydroxy group to a benzyloxy group which can eventually be removed by catalytic hydrogenation. Moreover, as indicated, it may be appropriate for a substituent group in the initially formed 3-hydroxypyridin-4-one to be modified to provide the desired substituents.

Salts may readily be formed by reaction of the compound (I) with the appropriate base or acid under suitable conditions. Thus, freeze drying of an aqueous solution whose pH has been adjusted to about 11 with the desired base provides a convenient route to a salt of that base containing an anion formed by the loss of the 3-hydroxy group proton. Salts with acids may conveniently be obtained by recrystallization of the compound (I) from an aqueous/organic solution, for example the hydrochloride being obtained on recrystallization from a dilute hydrochloric acid/ethanol solution. Pro-drugs may similarly be formed by reaction of the compound (I) or a derivative thereof with the appropriate reagent.

Thus, in general, the 3-hydroxypyridin-4-ones of use in the present invention may conveniently be prepared by:

(a) reacting a 3-hydroxy-4-pyrone of formula (II)

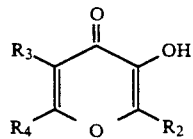

(II)

in which $R_2$ to $R_4$ correspond to the same groups as are present in the compound of formula (I), with a compound $R'NH_2$ in which $R'$ corresponds to the group $R_1$ in the compound of formula (I) or is a group convertible thereto;

(b) reacting a 3-hydroxypyridin-4-one of formula (III)

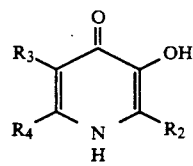

(III)

in which $R_2$ to $R_4$ correspond to the same groups as are present in the compound of formula (I), with a compound $R'X$ in which $R'$ corresponds to the group $R_1$ in the compound of formula (I) or is a group convertible thereto;

(c) reacting a 3-hydroxypyrid-4-one of formula (III) as defined in (b) with a compound $R'NH_2$ in which $R'$ corresponds to the group $R_1$ in the compound of formula (I) or is a group convertible thereto; or (d) treating a protected 3-hydroxypyridin-4-one of formula (IV)

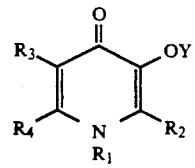

(IV)

in which $R_2$ to $R_4$ correspond to the same groups as are present in the compound of formula (I), $R_1$ corresponds to the group $R_1$ present in the compound of formula (I) or is a group convertible thereto and Y is a hydroxy protecting group, to remove the protecting group Y and thereby generate a hydroxy group; procedure (d) optionally being combined with one of procedures (a), (b) and (c) through the use of a compound of formula (II) or (III) in that procedure in which the hydroxy group thereof is in protected form as a group OY; and, where appropriate, in any procedure or combination of procedures, effecting the conversion of the group $R_1$ in the product to that present in the compound of formula (I) and/or converting the product to salt and/or pro-drug form.

The compounds (I) may be formulated with a physiologically acceptable diluent or carrier for use as pharmaceuticals for veterinary, for example in a mammalian context, and particularly for human use by a variety of methods. For instance, they may be applied as a composition incorporating a liquid diluent or carrier, for example an aqueous or oily solution, suspension or emulsion, which may often be employed in injectable form for parenteral administration and therefore may conveniently be sterile and pyrogen free. Oral administration may also be used, and indeed is preferred. Although compositions for this purpose may incorporate a liquid diluent or carrier, it is more usual to use a solid, for example a conventional solid carrier material such as starch, lactose, dextrin or magnesium stearate. Such solid compositions may conveniently be of a formed type, for example as tablets, capsules (including spansules), etc.

Other forms of administration than by injection or through the oral route may also be considered in both human and veterinary contexts, for example the use of suppositories or pessaries. Another form of pharmaceutical composition is one for buccal or nasal administration, for example lozenges, nose drops or an aerosol spray.

Thus, the invention further includes a pharmaceutical composition comprising a 3-hydroxypyridin-4-one of formula (I) as defined hereinbefore, but in which $R_2$ is ethyl, together with a physiologically acceptable diluent or carrier.

Compositions may be formulated in unit dosage form, i.e. in the form of discrete portions each comprising a unit dose, or a multiple or sub-multiple of a unit dose. Whilst the dosage of active compound given will depend on various factors, including the particular compound which is employed in the composition and the mode of administration and type of parasitic infection to be treated, it may be stated by way of guidance that satisfactory control of an iron dependent parasitic infection in the human body will often be achieved by maintaining a concentration of the compound in the bloodstream which provides a 10–50 $\mu M$ iron binding capacity (3 moles of the compound binding with 1 mole of iron). A dosage appropriate to provide such an iron binding capacity will usually lie in the region of about 0.5 or 1 g to 15 or 20 g daily, particularly of about 1 or 2 g to 10 or 15 g daily, for example about 5 g, veterinary doses being on a similar g/kg body weight ratio. However, it will be appreciated that it may be appropriate under certain circumstances to give daily dosages either below or above these levels, particularly the former with the more active compounds such as 3-hydroxy-1-(3-hydroxypropyl)-2-methylpyridin-4-one. Where desired, more than one compound according to the present invention may be administered in the pharmaceutical composition, when the total dosage will usually correspond to those discussed above, or, indeed, other active compounds may be included in the composition.

The compounds are of interest for the treatment of any condition caused by an iron dependent parasite, particularly those which infect erythrocytes. Such parasites include malaria and in particular those species of Plasmodium which infect the human such as *P. knowlesii* and also *P. vivax*, *P. ovale* and *P. malarias* but particularly *P. falciparum*. Other parasites which may be specifically mentioned are the causative agents of babesiosis, which are various species of Babesia such as *B. divergens*, and of tryponosomiasis, which are various species of Trypanosoma such as *I. croezi*.

It will be appreciated that the compounds may well be more effective against the parasite at one particular stage of its cell cycle than at others, as indeed is found to be the case with malaria where it has been found that control of the parasite is maximal at the late trophozoite and early schizont stages of the development of the parasite. However, since the life cycle of the parasite is usually relatively short, for example about 48 hours for *P. falciparum* in the human, then it is simplest to continue the period of treatment so that a suitable concentration of the compound in the bloodstream, as discussed hereinbefore, is maintained at least for the duration of the parasite cell cycle and conveniently for about 4 or 5 such cycles, i.e. for a period of about 7 to 10 days. This will usually require a daily dosage as indicated hereinbefore although it will be appreciated that for compounds with a long half life it may be possible to reduce the frequency of administration of the compound from a daily dosage.

The invention is illustrated by the following Examples.

EXAMPLES

Example 1

Preparation of
2-ethyl-3-hydroxy-1-(3-hydroxypropyl)-pyridin-4-one hydrochloride (1) 3-Benzyloxy-2-ethyl-4-pyrone To a stirred mixture of 2-ethyl-3-hydroxy-4-pyrone (49 g, 0.35 mol) in methanol (600 ml) and sodium hydroxide (16 g, 0.4 mol) dissolved in water (50 ml) was added benzyl chloride (47.2 ml, 0.41 mol) dropwise at room temperature. After heating under reflux for 48 hours the reaction mixture was cooled, filtered and the filtrate rotary evaporated to provide an oil. The oil was extracted with dichloromethane (300 ml), the solution washed with 5% w/v sodium hydroxide solution (3×250 ml) and water (3×250 ml), then dried over anhydrous sodium sulphate, filtered and rotary evaporated to provide an oil which was dissolved in diethyl ether and crystallized by coating with liquid nitrogen. Recrystallization from diethyl ether gave the title compound as colourless crystals (52.5 g, 65%), m.p. 33°–34° C.

(2) 3-Benzyloxy-2-ethyl-1-(3-hydroxpropyl)pyridin-4-one hydrochloride

To a stirred mixture of 3-benzyloxy-2-ethyl-4-pyrone (46 g, 0.2 mol) in a mixture of ethanol (500 ml), water (500 ml) and 3-amino-propan-1-ol (25 ml, 0.32 mol) was added 10M sodium hydroxide solution until the mixture reached pH 13. After heating the resulting suspension under reflux for 48 hours the ethanol was removed by rotary evaporation. The aqueous solution was adjusted to pH 7 by adding concentrated hydrochloric acid and was extracted with dichloromethane (3×150 ml). The organic extracts were dried over anhydrous sodium sulphate, filtered and rotary evaporated to give a product in the form of a yellow oil which was obtained as hydrochloride salt from ethanol and hydrochloric acid. Recrystallization from ethanol-diethyl ether yielded the hydrochloride title compound as white crystals (45.8 g, 71%), m.p. 138°–139° C.

(3) 2-Ethyl-3-hydroxy-1-(3-hydroxypropyl)pyridin-4-one hydrochloride

To a suspension of the hydrochloride salt of 3-benzyloxy-2-ethyl-(1-3-hydroxypropyl)pyridin-4-one (16.2 g, 0.05 mol) in ethanol (125 ml) and water (25 ml) was added 5% palladium on charcoal catalyst (1.6 g). The mixture was stirred under a constant stream of hydrogen for 4 hours at room temperature. After removal of the used catalyst by filtration the mixture was boiled with activated charcoal for 5 minutes, filtered and rotary evaporated to provide an oil which solidified on cooling. Recystallization from ethanol-diethyl ether yielded the hydrochloride title compound as white crystals (11.2 g, 96%), m.p. 147°–148° C.; $\nu_{max}$ (nujl) 3430, 1630 cm$^{-1}$; δ(90 MHz; d$_6$DMSO) 8.5 (s, br, 3OH), 8.35 (d, 1H,), 7.45 (d, 1H), 4.45 (t, 2H), 3.49 (t, 2H), 3.0 (q, 2H), 1.95 (quintet, 2H), 1.2 (t, 3H).

Example 2

Preparation of
2-ethyl-3-hydroxy-1-(4-hydroxybutyl)-pyridin-4-one hydrochloride (1) 3-Benzyloxy-2-ethyl-1-(4-hydroxybutyl)pyridin-4-one hydrochloride To a stirred mixture of 3-benzyloxy-2-ethyl-4-pyrone (46 g, 0.2 mol) in a mixture of ethanol (500 ml), water (500 ml) and 4-aminobutan-1-ol (27.7 ml, 0.3 mol) was added 10M sodium hydroxide solution until the mixture reached pH 13. The resulting suspension was heated under reflux for 48 hours. Working up as described for 3-benzyloxy-2-ethyl-1-(3-hydroxypropyl)pyridin-4-one in Example 1(2) yielded the hydrochloride title compound as pale yellow crystals (41.11 g, 61%), m.p. 142°–143° C.

(2) 2-Ethyl-3-hydroxy-1-(4-hydroxybutyl)pyridin-4-one hydrochloride

To a suspension of the hydrochloride salt of 3-benzyloxy-2-ethyl-1-(4-hydroxybutyl)pyridin-4-one (16.9 g, 0.05 mol) in a mixture of ethanol (125 ml) and water (25 ml) was added 5% palladium on charcoal catalyst (1.7 g). The mixture was stirred under a constant stream of hydrogen for 4 hours at room temperature. Working up as described for 2-ethyl-3-hydroxy-1-(3-hydroxypropyl)-pyridin-4-one in Example 1(3) yielded the hydrochloride title compound as white crystals (12.1 g, 98%), m.p. 165.4°–166.5° C; $\nu_{max}$ (nujol) 3440, 1630 cm$^{-1}$; δ(90 MHz; d$_6$DMSO) 9.4 (s, br, 3OH), 8.53 (d, 1H), 7.55 (d, 1H), 4.49 (t, 2H), 3.5 (t, 2H), 3.0 (q, 2H), 1.9 (quintet, 2H), 1.6 (quintet, 2H), 1.25 (t, 3H).

Note The 2-methyl analogues of the compounds of Examples 1 and 2 were obtained by an analogous procedure, these hydrochlorides having the melting points 160°–161° C. and 144°–145° C., respectively.

Example 3

Formulation of medicaments (A) Tablets of the following composition are prepared:

|  | mg/tablet |
|---|---|
| 3-hydroxy-1-(3-hydroxypropyl)-2-methylpyridin-4-one hydrochloride (micronised) | 250 |
| 'Avicel' (microcrystalline cellulose) | 38 |
| polyvinylpyrrolidone | 3 |
| alginic acid | 6 |
| magnesium stearate | 3 |

The 3-hydroxypyridin-4-one is mixed with 'Avicell' and polyvinylpyrrolidone is added, dissolved in sufficient industrial methylated spirits (74°OP) to produce a mass suitable for granulating. The mass is granulated through a 20 mesh sieve and the resultant granules are dried at a temperature not exceeding 50° C. The dried granules are passed through a 20 mesh sieve and the alginic acid and magnesium stearate are then added and mixed with the granules. The product is compressed into tablets each weighing 300 mg on ⅜ inch flat bevelled edge divided punches.

(B) Tablets of the following composition are prepared:

|  | mg/tablet |
|---|---|
| 3-hydroxy-1-(3-hydroxypropyl)-2-methylpyridin-4-one hydrochloride (micronised) | 250 |
| 'Avicel' (microcrystalline cellulose) | 134 |
| polyvinylpyrrolidone | 4 |
| alginic acid | 8 |
| magnesium stearate | 4 |

The tablets are prepared by essentially the same procedure as described in (A) and are compressed at a tablet weight of 400 mg on 7/16 inch flat bevelled edge punches.

(C) Tablets of the following composition are prepared:

|  | mg/tablet |
|---|---|
| 3-hydroxy-1-(3-hydroxypropyl)-2-methylpyridin-4-one hydrochloride (micronised) | 250 |
| lactose (300 mesh) | 19 |
| maize starch | 15 |
| gelatine | 10 |
| magnesium stearate | 6 |

The 3-hydroxypyridin-4-one is mixed with lactose and half the total quantity of maize starch required, and a 5% solution of gelatine in water is added to the mass. The product is granulated through a 16 mesh sieve, and the resultant granules are dried to constant weight at a temperature not exceeding 50° C. The dried granules are passed through a 20 mesh sieve and mixed with magnesium stearate and the remainder of the maize starch. The product is compressed at a 300 mg tablet weight on ⅜ inch flat bevelled edge divided punches.

Similar procedures may be followed with other compounds such as those of Examples 1 and 2 and the second compound of the footnote to Example 2.

We claim:

1. A method for the treatment of a patient having a condition caused by an iron dependent parasite which comprises administering to that patient a therapeutically effective amount of a 3-hydroxypyridin-4-one of formula (I)

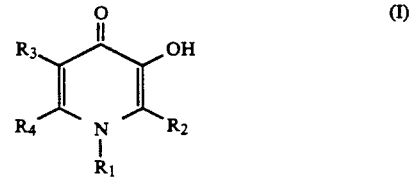

in which $R_1$ is a $C_3$ or $C_4$ hydroxyalkyl group in which the hydroxy group is terminally substituted on the alkyl group, $R_2$ is methyl or ethyl and $R_3$ and $R_4$ are each separately hydrogen, methyl or ethyl but with the proviso that the total number of carbon atoms in $R_1$ to $R_4$ is no more than six, the compound optionally being in the form of a physiologically acceptable salt and/or pro-drug thereof.

2. A method according to claim 1, in which $R_3$ and $R_4$ are each hydrogen.

3. A method according to claim 1, in which $R_2$ is methyl.

4. A method according to claim 1, in which $R_1$ is a $C_3$ hydroxyalkyl group.

5. A method according to claim 1, in which $R_1$ is a straight chain hydroxyalkyl group.

6. A method according to claim 1, in which $R_1$ is 3-hydroxypropyl.

7. A method according to claim 1, in which the compound of formula (I) is 3-hydroxy-1-(3-hydroxypropyl)-2-methylpyridin-4-one.

8. A method according to claim 1, in which the compound of formula (I) is 3-hydroxy-1-(4-hydroxybutyl)-2-methylpyridin-4-one.

9. A method according to claim 1, in which the compound of formula (I) is 2-ethyl-3-hydroxy-1-(3-hydroxypropyl)pyridin-4-one or 2-ethyl-3-hydroxy-1-(4-hydroxybutyl)pyridin-4-one.

10. A method according to claim 1, in which the patient has malaria.

* * * * *